United States Patent [19]

Caskey

[11] Patent Number: 5,575,989
[45] Date of Patent: Nov. 19, 1996

[54] POWDER BLEACHING COMPOSITIONS FOR HAIR AND METHOD OF USE THEREOF

[75] Inventor: Paul F. Caskey, Sussex, N.J.

[73] Assignee: CCP, Inc., West Patterson, N.J.

[21] Appl. No.: 294,437

[22] Filed: Aug. 23, 1994

Related U.S. Application Data

[63] Continuation of Ser. No. 10,420, Jan. 28, 1993, abandoned.

[51] Int. Cl.$^6$ .............................. A61K 7/135; A61K 7/06
[52] U.S. Cl. ..................... 424/62; 424/DIG. 3; 132/208
[58] Field of Search ................................ 424/70.2, 70.1, 424/62, DIG. 3; 132/208

[56] References Cited

U.S. PATENT DOCUMENTS

| | | | |
|---|---|---|---|
| 3,378,444 | 4/1968 | Swanson | 424/62 |
| 3,480,557 | 11/1969 | Shiraeff | 252/186 |
| 3,726,967 | 4/1973 | Vorsatz et al. | 424/62 |
| 3,816,614 | 6/1974 | Zeffren et al. | 424/62 |
| 3,898,032 | 8/1975 | Edman et al. | 8/10.2 |
| 4,170,637 | 10/1979 | Pum | 424/62 |
| 4,247,537 | 1/1981 | Lunn et al. | 424/62 |
| 4,313,932 | 2/1982 | Watts | 424/62 |
| 4,507,278 | 3/1985 | DeMarco et al. | 424/62 |
| 4,927,627 | 5/1990 | Schrader | 424/62 |
| 5,064,441 | 11/1991 | Kawase et al. | 8/405 |
| 5,116,388 | 5/1992 | Brooks | 8/405 |
| 5,294,936 | 3/1994 | Cope et al. | 424/62 |

FOREIGN PATENT DOCUMENTS

| | | | |
|---|---|---|---|
| 0033687 | 8/1981 | European Pat. Off. | 424/62 |

*Primary Examiner*—Sallie M. Gardner
*Attorney, Agent, or Firm*—Cooper & Dunham LLP

[57] ABSTRACT

The invention relates to a powder bleaching composition for bleaching hair or keratinous fiber and methods for the production and use of the composition. The powder bleaching composition comprises a conditioner of about 2% to about 15% by weight of said composition, a bleach accelerator of about 40% to about 60% by weight of said composition, a thickener of about 1% to about 10% by weight of said composition, a silica component of about 2% to about 11% by weight of said composition, and a hydrogen peroxide source of about 15% to about 23% by weight of said composition, with a sufficient amount of water to provide a water-activated composition. The above composition prevents damage to the hair during bleaching and provides limited ammonia odor during use.

14 Claims, No Drawings

POWDER BLEACHING COMPOSITIONS FOR HAIR AND METHOD OF USE THEREOF

This application is a continuation of Ser. No. 08/010,420 filed Jan. 28, 1993, now abandoned.

BACKGROUND OF THE INVENTION

1. Field of the Invention

This invention relates to water-activated powder compositions for improved hair bleaching.

2. Description of the Prior Art

It is well known to use hydrogen peroxide as a bleaching agent on hair. However, the use of hydrogen peroxide has the disadvantage that it does not penetrate the hair follicle. In addition hydrogen peroxide has the disadvantage of irritating sensitive scalps.

Activating compounds have been added to hydrogen peroxide for improving the penetration of bleach into the hair follicle. These liquid compositions have disadvantages such as poor shelf life and expensive shipping characteristics.

A conventional solution for eliminating the need for hydrogen peroxide is to use a dry composition which produces hydrogen peroxide when water activated. U.S. Pat. No. 4,313,932 describes a composition which forms a hair bleaching solution when mixed with water. A hydrogen peroxide producer compound is used which releases or generates hydrogen peroxide when dissolved in water and is a solid when dry. An ammonium compound in addition to a bleach accelerator is used which generates ammonium ions when dissolved in water. A thickener of finely divided silica and dried acrylic polymer latex or a homo- or copolymer of acrylamide produces desired viscosity of the solution. A bleach accelerator selected from alkali metal and either ammonium peroxydisulfates or peroxydiphosphates acts as a booster for the bleaching action. The 4,313,932 patent has the disadvantage that the use of an alkali metal accelerator may cause damage to the hair and that the use of an additional ammonium compound increases ammonia odor.

U.S. Pat. No. 4,247,537 describes a bleaching powder in a vapor proof enclosure which is capable upon aqueous activation of bleaching hair or keratinous fiber. The bleaching composition includes at least 25% by weight of ammonium persulfate, at least 25% by weight of sodium percarbonate or potassium percarbonate and at least 4 to 10% of pyrogenic silica. A two step mixing process is used for premixing the ammonium persulfate with a portion of pyrogenic silica and mixing the percarbonate compound with the remaining portion of pyrogenic silica prior to the whole composition being mixed together. The composition of this patent using at least 25% sodium percarbonate has the disadvantage that the hair may lose its normal resilience and the hair may become dry and brittle. In addition the use of at least 25% of ammonium persulfate releases an undesirable ammonia odor. Also, the use of at least 4% pyrogenic silica increases the likelihood that the bleach will dry on the head and flake off onto the face or into the eyes.

Of possible general relevance are U.S. Pat. No. 3,726,967 related to a dry free flowing bleaching composition and U.S. Pat. No. 5,064,441 relate to a solid stabilized hydrogen peroxide composition.

Common complaints by salon owners and operators are of undesirable high levels of ammonia odors and damage to the hair. A stable water-activated powder composition which prevents damage to the hair during bleaching and provides limited ammonia odor during use is desirable in the cosmetic industry.

SUMMARY OF THE INVENTION

The present invention relates to a powder composition for bleaching of hair or keratinous fiber and a method for the preparation thereof comprising a conditioner. A conditioner of about 2% to about 15% by weight of said composition, a bleach accelerator of about 40% to about 60% by weight of said composition, a thickener of about 1% to about 10% by weight of said composition, a silica component of about 2% to about 11% by weight of said composition, and a hydrogen peroxide source of about 15% to about 23% by weight of said composition, with a sufficient amount of water to provide a water-activated composition. Preferably, the particle size of the final powder composition is less than 20 mesh.

The present invention further relates to a method of bleaching hair or keratinous fiber comprising the steps of mixing an amount of the above powder composition with sufficient water to provide a water-activated composition, applying the water-activated composition to hair or keratinous fiber and removing the applied water-activated composition from the hair or keratinous fiber.

The powder bleaching composition of the present invention advantageously minimizes damage or prevents excess damage to the hair during bleaching and provides limited ammonia odor during use.

DETAILED DESCRIPTION OF THE INVENTION

The novel hair bleaching compositions of the present invention are stable water-activated powders which bleach reduces unwanted odors and damage to the hair. Preferably, the powder bleaching composition includes a conditioner, a bleach accelerator, a thickener, silica and a peroxide source.

Conditioners that can be utilized in the present invention condition hair without hindering bleaching activity. The proportion of the conditioner that is added to the powder bleaching composition is from about 2 to about 15% by weight of the powder bleaching composition. Preferably, aluminum stearate, sodium stearate, magnesium stearate, or mixtures thereof can be used as conditioners. Protein compounds such as hydrolyzed collagen also can be employed as conditioners. While other organic compounds can be used as conditioners, these compounds should be evaluated for stability in the powder bleaching composition.

A bleach accelerator promotes the bleaching action of the hydrogen peroxide generated when the powder bleaching composition is mixed with water. Ammonium persulfate, potassium persulfate or sodium persulfate and mixtures thereof can be used in a concentration of about 40 to about 60% by weight of the powder bleaching composition. It is preferable to minimize the use of ammonium persulfate to reduce the ammonia odor from the water-activated bleaching composition. Therefore, it is preferable to use less ammonium persulfate and substitute therefor potassium persulfate or sodium persulfate. Preferably, ammonium persulfate forms about 10 to about 15% by weight of the powder bleaching composition and potassium persulfate or sodium persulfate forms about 25 to about 50% by weight of the powder bleaching composition.

Thickeners utilized in the present invention enhance viscosity which prevents the water-activated bleaching composition from running off of the head during bleaching and aids in suspending components of the powder bleaching composition. Thickeners also allow the loading of a sufficient amount of water into the bleaching system to drive the reaction and release hydrogen peroxide for suitable bleaching. The powder bleaching composition includes about 1 to about 10% thickener by weight of the powder bleaching composition. Preferably, hydroxypropyl methylcellulose, hydroxyethylcellulose and mixtures thereof are used as thickeners. Algin and organic gums such as cellulose gums or xanthan gums can also be employed as thickeners. Sodium metasilicate can be added in addition to the above-described thickeners.

A silica component is used in the powder bleaching composition as an anti-caking agent and a desiccant agent. The silica component can be used in concentrations of about 2 to about 11% of the powder bleaching composition. Preferably, hydrated silica in an amount of about 1 to about 8% of the powder bleaching composition and silica in an amount of about 1 to about 3% of the powder bleaching composition are used. The use of hydrated silica and the concurrent reduction of silica reduces the potential for the water-activated composition to dry out after application to the hair.

A hydrogen peroxide source releases the hydrogen peroxide upon water-activation which is required to bleach hair. The hydrogen peroxide source forms about 15 to about 23% of the powder bleaching composition. Preferred peroxide sources are sodium percarbonate and potassium percarbonate. The hydrogen peroxide source can also be a perhydrate such as sodium phosphate perhydrate and sodium carbonate perhydrate. It will be appreciated that other hydrogen peroxide sources known in the art for releasing hydrogen peroxide can be used.

A surfactant can be used in the powder bleaching composition in a concentration of about 0.5 to about 4% of the powder bleaching composition. Surfactants useful in the present invention are sodium lauryl sulfate and ammonium lauryl sulfate. It will be appreciated that other surfactants known in the art can be used in the powder bleaching composition.

In addition, a chelating agent can be included in the powder bleaching composition. Preferably, ethylenediaminetetraacetic acid (EDTA) can be employed in a concentration of about 0.5 to about 5.0% of the powder bleaching composition.

Sugar can be used as a humectant to retain moisture in the hair and prevent drying out. Preferably, sugar is used in a concentration of about 0 to about 2% of the powder bleaching composition.

Fragrance can be added to the powder bleaching composition for enhancing the cosmetic appeal of the bleach. The fragrance helps to mask the minimal ammonia odor released from the water-activated bleaching composition. Preferably, fragrance is used in a concentration of about 0.5 to about 3% of the powder bleaching composition.

The powder bleaching compositions are formulated by blending the components in a suitable vessel. Preferably, the components are added sequentially according to known practices in the cosmetic art. The optional fragrance component can be added by spraying on the final powder bleaching composition, or by incorporating the fragrance component into one of the other components or by blending the fragrance component with the other components. It will be appreciated that other methods known in the art can be used for adding the fragrance.

The powder bleaching composition of the present invention is preferably formed of particles which are sufficiently fine so that no large crystals or agglomerates, known as "hot spots", accumulate on hair to cause uneven bleaching or scalp burns, and the particles are sufficiently large so that the powder bleaching composition is not fine dust. Preferably, the particle size of the powder bleaching composition is less than 20 mesh. The final powder bleaching composition can be milled or in the alternative components having a particle size of less than 20 mesh can be used in forming the composition. A secondary mixing process can be used after the milling process to re-mix those ingredients which may have stratified as a result of milling.

The powder bleaching composition can be used to bleach human hair or other keratinous fiber. The hair bleaching composition after activation with water forms a bleach which can achieve 1–7 levels of lift. The bleached hair has a smooth appearance and is uniformly bleached. The powder bleaching composition can also be used for lifting deposited color out of hair in order to prepare the hair for re-dyeing. The powder bleaching composition is advantageous for use in perming hair after bleaching.

A water-activated bleach composition is preferably prepared by mixing 1 part of the powder bleaching composition with 1 or 2 parts of water in a conventional manner such as in a non-metal bowl. The solution is allowed to stand for at least one minute to achieve a suitable viscosity of the water-activated composition. The water-activated composition is applied to the hair in a conventional manner. Heat can be applied to the hair after application of the water-activated composition to accelerate bleaching. Suitable heat sources include hair dryers and heat lamps. The applied water-activated composition can be removed from the hair by rinsing with water or shampoo.

The following examples will serve to further typify the nature of this invention but should not be construed as a limitation on the scope thereof, which scope is defined solely by the appended claims.

EXAMPLE 1

| INGREDIENT | AMOUNT (g) |
| --- | --- |
| Magnesium Stearate | 3.0 |
| Cellulose Gum | 3.0 |
| Algin | 2.0 |
| Hydrolyzed Collagen | 4.0 |
| Hydrated Silica | 4.0 |
| Ammonium Persulfate | 20.0 |
| Silica | 1.5 |
| Hydroxypropyl Methylcellulose | 10.0 |
| Sodium Percarbonate | 21.0 |
| Potassium Persulfate | 31.5 |
| | 100.0 |

The foregoing ingredients are blended in a suitable vessel. The resulting mixture is milled to yield particles of a size less than 20 mesh.

EXAMPLE 2

| INGREDIENT | AMOUNT (g) |
| --- | --- |
| Aluminum Stearate | 4.0 |
| Ammonium Persulfate | 20.0 |
| Ethylenediaminetetraacetic Acid (EDTA) | 0.5 |
| Hydroxyethylcellulose | 3.5 |
| Potassium Persulfate | 46.0 |
| Silica | 2.0 |
| Sodium Stearate | 5.0 |
| Hydrated Silica | 2.0 |
| Sodium Lauryl Sulfate | 2.0 |
| Sodium Percarbonate | 15.0 |
| | 100.0 |

The foregoing ingredients are blended in a suitable vessel. The resulting mixture is milled to yield particles of a size less than 20 mesh.

EXAMPLE 3

The powder bleaching composition produced in Example 2 is mixed with water in a ratio of from 1:1 to 1:2 (composition:water) in a non-metal bowl. After allowing the water-activated composition to set for about one minute to achieve a suitable viscosity, a strand test is performed on the human subject's hair to determine (and thus correct for) any intersubject variability in time required for lift. The water-activated composition then is applied to the subject's hair and the subject is placed under a hair dryer for approximately 20 minutes. The water-activated composition is removed from the hair by rinsing with water.

The treated hair is smooth and uniformly bleached.

While the invention has been described with reference to the preferred embodiment thereof, it will be appreciated by those of ordinary skill in the art that modifications can be made to the structure and elements of the invention without departing from the spirit and scope of the invention as a whole.

I claim:

1. A powder composition for bleaching of human hair comprising:

a conditioner of about 2% to about 15% by weight of the powder composition, the conditioner selected from the group consisting of aluminum stearate, sodium stearate, magnesium stearate, hydrolyzed collagen and mixtures thereof;

a bleach accelerator of about 40% to about 60% by weight of the powder composition, the bleach accelerator comprising 25–50% by weight of the of the powder composition of potassium persulfate and 10–15% by weight of the powder composition of ammonium persulfate;

a thickener of about 1% to about 10% by weight of the powder composition;

a silica component of about 2% to about 11% by weight of the powder composition; and a hydrogen peroxide source of about 15% to about 23% by weight of the powder composition, the hydrogen peroxide source comprising sodium percarbonate.

2. The composition of claim 1 wherein said bleach accelerator further comprises sodium persulfate.

3. The composition of claim 1 wherein said thickener is selected from the group consisting of hydroxypropyl methylcellulose, hydroxyethylcellulose, algin, gums, sodium metasilicate, and mixtures thereof.

4. The composition of claim 1 wherein said silica component is selected from the group consisting of hydrated silica, silica and mixtures thereof.

5. The composition of claim 4 wherein said hydrated silica forms about 1% to about 8% of said composition and said silica forms about 1% to about 3% of said composition.

6. The composition of claim 1 further comprising a surfactant in an amount of about 0.5% to about 4% by weight of said composition.

7. The composition of claim 1 further comprising a sugar in an amount of 2% or less by weight of said composition.

8. The composition of claim 1 further comprising a fragrance.

9. A method of bleaching human hair, comprising the steps of:

mixing an amount of a hair bleaching powder composition, the hair bleaching powder composition comprising: a conditioner of about 2% to about 15% by weight of the hair bleaching powder composition selected from the group consisting of aluminum stearate, sodium stearate, magnesium stearate, hydrolyzed collagen and mixtures thereof; a bleach accelerator including about 10% to about 15% ammonium persulfate and about 25% to about 50% potassium persulfate by weight of the hair bleaching powder composition; a thickener of about 1% to about 10% by weight of the hair bleaching powder composition; a silica component of about 2% to about 11% by weight of the hair bleaching powder composition; and a hydrogen peroxide source of about 15% to about 23% by weight of the hair bleaching powder composition comprising sodium percarbonate; with a sufficient amount of water to provide a water-activated composition;

applying the water-activated composition to a user's hair; and removing the applied water-activated composition from the hair.

10. The method of claim 9 further comprising the step of:

heating said water-activated composition after the step of applying said water-activated composition to said hair.

11. A method for preparing a powder composition for bleaching hair or keritinous fiber comprising the step of:

mixing a conditioner selected from the group consisting of aluminum stearate, sodium stearate, magnesium stearate, hydrolyzed collagen, and mixtures thereof of about 2% to about 15% by weight of said composition, a bleach accelerator of about 40% to about 60% by weight of said composition comprising 25–50% by weight of the of the powder composition of potassium persulfate and 10–15% by weight of the powder composition of ammonium persulfate, a thickener of about 1% to about 10% by weight of said composition, a silica component of about 2% to about 11% by weight of said composition, and a hydrogen peroxide source comprising sodium percarbonate of about 15% to about 23% by weight of said composition.

12. The method of claim 11 wherein said conditioner, said bleach accelerator, said thickener, said silica component and said hydrogen peroxide source are mixed sequentially.

13. The method of claim 11 further comprising the step of grinding said formed composition to a particle size of less than 20 mesh.

14. The method of claim 11 wherein said conditioner, said bleach accelerator, said thickener, said silica component and said hydrogen peroxide source have a particle size of less than 20 mesh.

* * * * *